United States Patent
Rana et al.

(10) Patent No.: US 12,164,870 B2
(45) Date of Patent: Dec. 10, 2024

(54) METHOD AND SYSTEM FOR NEURAL DOCUMENT EMBEDDING BASED ONTOLOGY MAPPING

(71) Applicant: Tata Consultancy Services Limited, Mumbai (IN)

(72) Inventors: Sadhna Rana, Bhubaneswar (IN); Rajgopal Srinivasan, Hyderabad (IN); Swatantra Pradhan, Bhubaneswar (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 287 days.

(21) Appl. No.: 17/934,258

(22) Filed: Sep. 22, 2022

(65) Prior Publication Data
US 2023/0124230 A1    Apr. 20, 2023

(30) Foreign Application Priority Data
Oct. 14, 2021   (IN) .............................. 202121047011

(51) Int. Cl.
*G06F 40/247*   (2020.01)
*G06F 40/205*   (2020.01)
*G06F 40/40*    (2020.01)

(52) U.S. Cl.
CPC .......... *G06F 40/247* (2020.01); *G06F 40/205* (2020.01); *G06F 40/40* (2020.01)

(58) Field of Classification Search
CPC ...... G06F 40/247; G06F 40/205; G06F 40/40; G06F 40/30; G06N 3/088; G06N 5/022; G06N 3/045; G16H 50/20; G16H 50/70
See application file for complete search history.

(56) References Cited

U.S. PATENT DOCUMENTS

| 11,921,769 B2 * | 3/2024 | Tonkin ................... G06F 16/328 |
| 2017/0004208 A1 * | 1/2017 | Podder .................... G06F 40/30 |

(Continued)

FOREIGN PATENT DOCUMENTS

| EP | 3127020 | 2/2017 |
| WO | WO2015149114 A1 | 8/2015 |

OTHER PUBLICATIONS

Yuanzhe Zhang et al., Ontology Matching with Word Embeddings, Computer Science, 2014, Springer, http://cips-cl.org/static/anthology/CCL-2014/CCL-14-074.pdf.

(Continued)

*Primary Examiner* — Fariba Sirjani
(74) *Attorney, Agent, or Firm* — FINNEGAN, HENDERSON, FARABOW, GARRETT & DUNNER LLP (57) ABSTRACT

The present disclosure provides a neural document embedding based ontology mapping. Conventional methods that map ontology concepts across domains/species extensively take help of bridging ontologies. Initially the system receives a Human Phenotype (HP) Identification number (ID) pertaining to a phenotype. A first HP ID vector is computed from the HP ID using a trained word2vec model. A second HP ID vector is computed from the HP ID using a trained Doc2vec model. An average HP ID vector is computed based on the first HP ID vector and the second HP ID vector. A plurality of cosine similarity scores are computed based on a comparison between the average HP ID vector and a plurality of average MP ID vectors. The plurality of MP IDs are sorted based on the plurality of cosine similarity scores. The plurality of MP IDs corresponding to the HP ID are selected based on a selection threshold.

20 Claims, 5 Drawing Sheets

(56) References Cited

U.S. PATENT DOCUMENTS

| | | | | |
|---|---|---|---|---|
| 2017/0185674 | A1* | 6/2017 | Tonkin | G06F 16/367 |
| 2018/0082197 | A1* | 3/2018 | Aravamudan | G16B 50/00 |
| 2020/0192727 | A1* | 6/2020 | Savenkov | G06F 9/547 |
| 2020/0372057 | A1* | 11/2020 | Tonkin | G06F 16/367 |
| 2020/0379958 | A1* | 12/2020 | Riggs | G06F 16/2358 |
| 2022/0035817 | A1* | 2/2022 | Carrier | G06F 40/30 |
| 2022/0035866 | A1* | 2/2022 | Carrier | G06F 16/90332 |
| 2022/0058562 | A1* | 2/2022 | Swaminathan | G06F 16/958 |
| 2022/0148679 | A1* | 5/2022 | Huettner | G16H 15/00 |
| 2022/0292123 | A1* | 9/2022 | Hoppe | G06F 16/35 |
| 2022/0398378 | A1* | 12/2022 | Wendell | G06F 16/33 |
| 2022/0414128 | A1* | 12/2022 | Raimondo | G06F 16/3344 |
| 2023/0039937 | A1* | 2/2023 | Wendell | G16H 15/00 |
| 2023/0117206 | A1* | 4/2023 | Venkateshwaran | G06Q 40/08 |
| | | | | 704/9 |
| 2023/0124230 | A1* | 4/2023 | Rana | G06N 3/088 |
| | | | | 704/9 |
| 2024/0046036 | A1 | 2/2024 | Garifullina | G06F 40/211 |
| 2024/0152542 | A1* | 5/2024 | Tonkin | G06F 16/367 |
| 2024/0249215 | A1* | 7/2024 | Swaminathan | G06Q 10/06398 |

OTHER PUBLICATIONS

Prodromos Kolyvakis et al. "Biomedical ontology alignment: an approach based on representation learning," Journal of Biomedical Semantics, 2018, Springer, https://jbiomedsem.biomedcentral.com/track/pdf/10.1186/s13326-018-0187-8.pdf.

Anika Oellrich et al. Quantitative comparison of mapping methods between Human and Mammalian Phenotype Ontology, Journal of Biomedical Semantics, 2012, Pubmed, https://jbiomedsem.biomedcentral.com/track/pdf/10.1186/2041-1480-3-S2-S1.pdf.

Pavel Shvaiko et al. "Ontology matching: state of the art and future challenges," Transactions on Knowledge and Data Engineering, 2013, vol. 25, Issue: 1, pp. 158-176, IEEE Link: https://hal.inria.fr/hal-00917910/document.

Ikechukwu Nkisi-Orji et al., "Ontology alignment based on word embedding and random forest classification," Machine Learning and Knowledge Discovery in Databases, 2018, Springer https://rgu-repository.worktribe.com/OutputFile/297608.

Aroua Essayeh et al., "Towards ontology matching based system through terminological, structural and semantic level," Procedia Computer Science, 2018, vol. 60, pp. 403-412, Science Direct, https://reader.elsevier.com/reader/sd/pii/S1877050915022814?token=388E040F58B35860BFB5A0C0622CD3F8038969B02FC6EE4FD6D1385C700085BD4A67C711A25C349077E57DDBD5266C79&originRegion=eu-west-1&originCreation=20220826101243.

* cited by examiner

METHOD AND SYSTEM FOR NEURAL DOCUMENT EMBEDDING BASED ONTOLOGY MAPPING

PRIORITY CLAIM

This U.S. patent application claims priority under 35 U.S.C. § 119 to: Indian Patent Application No. 202121047011, filed on Oct. 14, 2021. The entire contents of the aforementioned application are incorporated herein by reference.

TECHNICAL FIELD

The disclosure herein generally relates to the field of Natural Language Processing (NLP) and, more particular, to a method and system for neural document embedding based ontology mapping.

BACKGROUND

Ontologies are vital in annotating and organizing data in various domains in a machine readable format. In the field of biomedical sciences there are various ontologies each with its own context and applications. There are various types of ontologies like species specific phenotype ontologies such as Human Phenotype Ontology (HPO) and Mammalian Phenotype Ontology (MPO), species and developmental stage specific anatomical ontologies, such as Foundational Model of Anatomy (FMA) and Zebrafish Anatomy Ontology (ZFA) and human disease based ontologies such as disease ontology (DO) and SNOMED CT that differ in terms of coverage and structure. Since a single reference ontology provides insufficient coverage for translational applications in medicine, mapping methods are needed that can form inter ontological connections. The inter ontological connections can be within a particular domain or it can be across different domains, such as anatomy, disease and phenotypes. Thus, mapping algorithms can lead to identification of targets of higher importance for treatment of diseases.

Conventional methods that map ontology concepts across domains extensively take help of bridging ontologies. For example, Unified Medical Language System (UMLS) has served as a bridging ontology between DO and SNOMED CT for translational applications in Biomedicine. Similarly, Uberon ontology integrates different anatomical ontologies and phenotype ontologies by representing phenotypes in a species neutral way. These bridging ontologies are created using some defined axioms that help in mapping terms across ontologies and involve extensive manual curation. Hence there is a challenge in developing an automatic ontology mapping system without using bridging ontologies.

SUMMARY

Embodiments of the present disclosure present technological improvements as solutions to one or more of the above-mentioned technical problems recognized by the inventors in conventional systems. For example, in one embodiment, a method for neural document embedding based ontology mapping is provided. The method includes receiving, by one or more hardware processors, a Human Phenotype (HP) Identification number (ID) pertaining to a phenotype associated with a human disease from a user. Further, the method includes computing, by the one or more hardware processors, a first HP ID vector corresponding to the HP ID using a trained word2vec model, wherein the word2vec model is trained using a training corpus. Furthermore, the method includes simultaneously computing, by the one or more hardware processors, a second HP ID vector corresponding to the HP ID using a trained Doc2vec model, wherein the Doc2vec model is trained using the training corpus. Furthermore, the method includes computing, by the one or more hardware processors, an average HP ID vector based on the first HP ID vector and the second HP ID vector. Furthermore, the method includes computing, by the one or more hardware processors, a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID. Furthermore, the method includes sorting, by the one or more hardware processors, the plurality of MP IDs based on the plurality of cosine similarity scores in descending order. Finally, the method includes displaying, by the one or more hardware processors, the plurality of MP IDs corresponding to the HP ID to the user by selecting a plurality of sorted MP IDs based on a predetermined selection threshold.

In another aspect, a system for neural document embedding based ontology mapping is provided. The system includes at least one memory storing programmed instructions, one or more Input/Output (I/O) interfaces, and one or more hardware processors operatively coupled to the at least one memory, wherein the one or more hardware processors are configured by the programmed instructions to receive a Human Phenotype (HP) Identification number (ID) pertaining to a phenotype associated with a human disease from a user. Further, the one or more hardware processors are configured by the programmed instructions to compute a first HP ID vector corresponding to the HP ID using a trained word2vec model, wherein the word2vec model is trained using a training corpus. Furthermore, the one or more hardware processors are configured by the programmed instructions to compute a second HP ID vector corresponding to the HP ID using a trained.

Doc2vec model, wherein the Doc2vec model is trained using the training corpus. Furthermore, the one or more hardware processors are configured by the programmed instructions to compute an average HP ID vector based on the first HP ID vector and the second HP ID vector. Furthermore, the one or more hardware processors are configured by the programmed instructions to compute a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID. Furthermore, the one or more hardware processors are configured by the programmed instructions to sort the plurality of MP IDs based on the plurality of cosine similarity scores in descending order. Finally, the one or more hardware processors are configured by the programmed instructions to display the plurality of MP IDs corresponding to the HP ID to the user by selecting a plurality of sorted MP IDs based on a predetermined selection threshold.

In yet another aspect, a computer program product including a non-transitory computer-readable medium having embodied therein a computer program for neural document embedding based ontology mapping is provided. The computer readable program, when executed on a computing device, causes the computing device to receive a Human Phenotype (HP) Identification number (ID) pertaining to a phenotype associated with a human disease from a user. Further, the computer readable program, when executed on a computing device, causes the computing device to compute a first HP ID vector corresponding to the HP ID using a trained.

word2vec model, wherein the word2vec model is trained using a training corpus. Furthermore, the computer readable program, when executed on a computing device, causes the computing device to compute a second HP ID vector corresponding to the HP ID using a trained.

Doc2vec model, wherein the Doc2vec model is trained using the training corpus. Furthermore, the computer readable program, when executed on a computing device, causes the computing device to compute an average HP ID vector based on the first HP ID vector and the second HP ID vector. Furthermore, the computer readable program, when executed on a computing device, causes the computing device to compute a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID. Furthermore, the computer readable program, when executed on a computing device, causes the computing device to sort the plurality of MP IDs based on the plurality of cosine similarity scores in descending order. Finally, the computer readable program, when executed on a computing device, causes the computing device to display the plurality of MP IDs corresponding to the HP ID to the user by selecting a plurality of sorted MP IDs based on a predetermined selection threshold.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

Embodiments herein provide a method and system for neural document embedding based ontology mapping for two different ontologies without bridging ontologies. Initially the system receives a Human Phenotype (HP) Identification number (ID) pertaining to a phenotype associated with a human disease from a user. A first HP ID vector corresponding to the HP ID is computed using a trained word2vec model, wherein the word2vec model is trained using a training corpus. Simultaneously a second HP ID vector corresponding to the HP ID is computed using a trained Doc2vec model, wherein the Doc2vec model is trained using the training corpus. Further an average HP ID vector is computed based on the first HP ID vector and the second HP ID vector. The computed average is used for computing a plurality of cosine similarity scores based on a comparison between the average HP ID vector and a plurality of average MP ID vectors corresponding to each of a plurality of Mammalian Phenotypes (MP), wherein each of the plurality of MPs are associated with a corresponding MP ID. After computing the cosine similarities, the plurality of MP IDs is sorted based on the plurality of cosine similarity scores in descending order. Finally, the plurality of MP IDs corresponding to the HP ID are displayed to the user by selecting a plurality of sorted MP IDs based on predetermined selection threshold.

Referring now to the drawings, and more particularly to FIGS. 1 through 4, where similar reference characters denote corresponding features consistently throughout the figures, there are shown preferred embodiments and these embodiments are described in the context of the following exemplary system and/or method.

Figure 1:
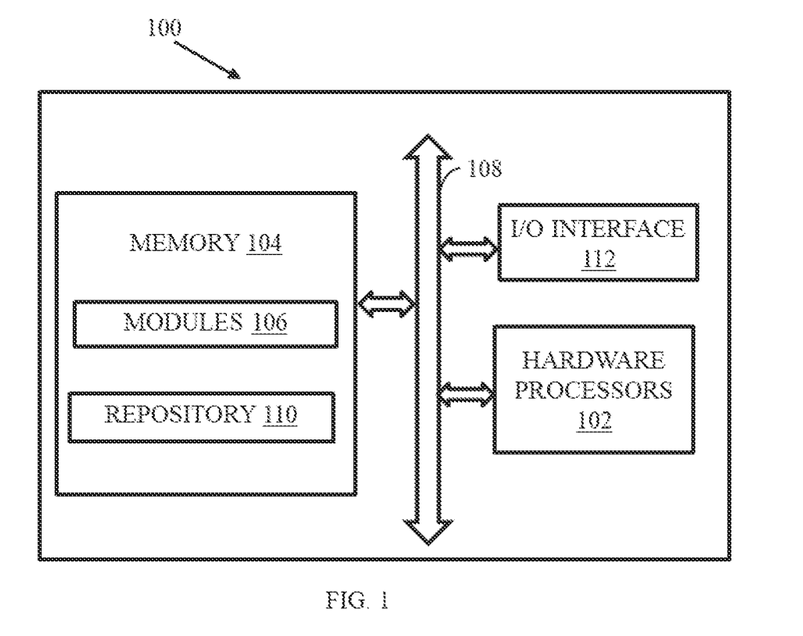
FIG. 1 is a functional block diagram of a system for neural document embedding based ontology mapping, in accordance with some embodiments of the present disclosure.

FIG. 1 is a functional block diagram of a system 100 for neural document embedding based ontology mapping, according to some embodiments of the present disclosure. The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a plurality of modules 106. The memory 104 also includes a data repository (or repository) 110 for storing data processed, received, and generated by the plurality of modules 106.

The plurality of modules 106 include programs or coded instructions that supplement applications or functions performed by the system 100 for neural document embedding based ontology mapping. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for neural document embedding based ontology mapping. In an embodiment, plurality of modules 106 includes a first HP ID computation module (not shown in FIG. 1), a second HP ID computation module (not shown in FIG. 1), an average HP ID computation module (not shown in FIG. 1), a cosine similarity computation module (not shown in FIG. 1), a sorting module (not shown in FIG. 1) and a MP ID displaying module (not shown in FIG. 1).

The data repository (or repository) 110 may include a plurality of abstracted piece of code for refinement and data that is processed, received, or generated as a result of the execution of the plurality of modules in the module(s) 106.

Although the data repository 110 is shown internal to the system 100, it will be noted that, in alternate embodiments, the data repository 110 can also be implemented external to the system 100, where the data repository 110 may be stored within a database (not shown in FIG. 1) communicatively coupled to the system 100. The data contained within such external database may be periodically updated. For example, new data may be added into the database (not shown in FIG. 1) and/or existing data may be modified and/or non-useful data may be deleted from the database (not shown in FIG. 1). In one example, the data may be stored in an external system, such as a Lightweight Directory Access Protocol (LDAP) directory and a Relational Database Management System (RDBMS).

Figure 2A:
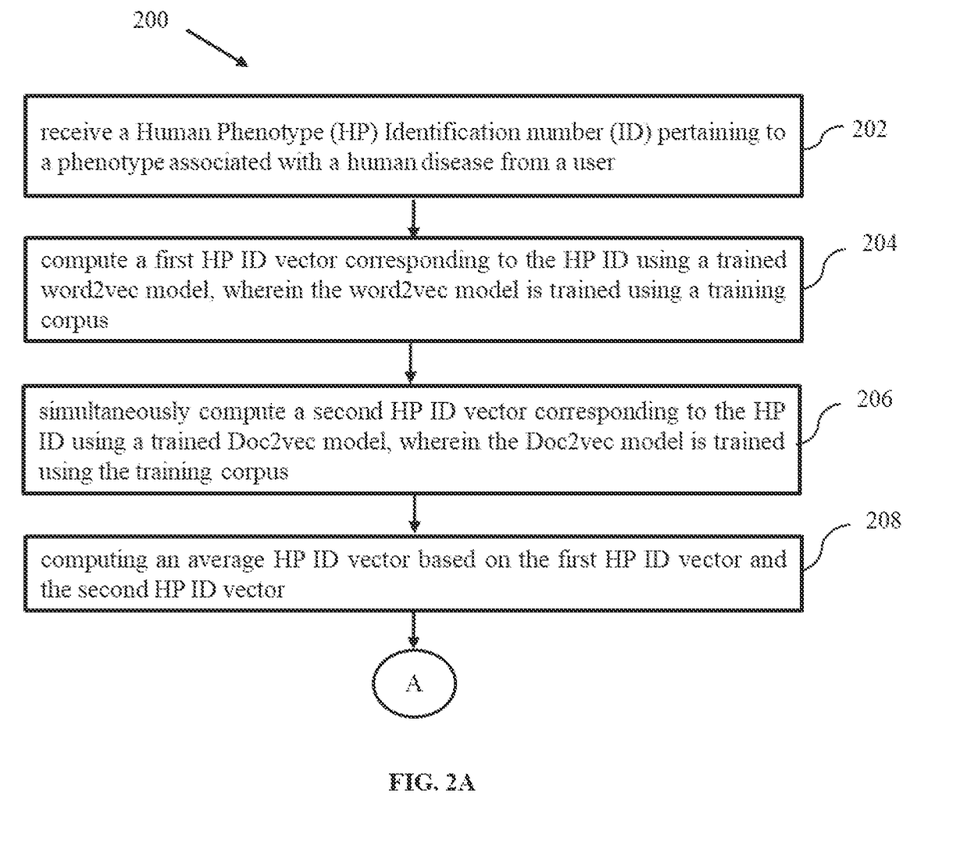
FIGS. 2A and 2B are exemplary flow diagrams illustrating a method for neural document embedding based ontology mapping, implemented by the system of FIG. 1, in accordance with some embodiments of the present disclosure.
Figure 2B:
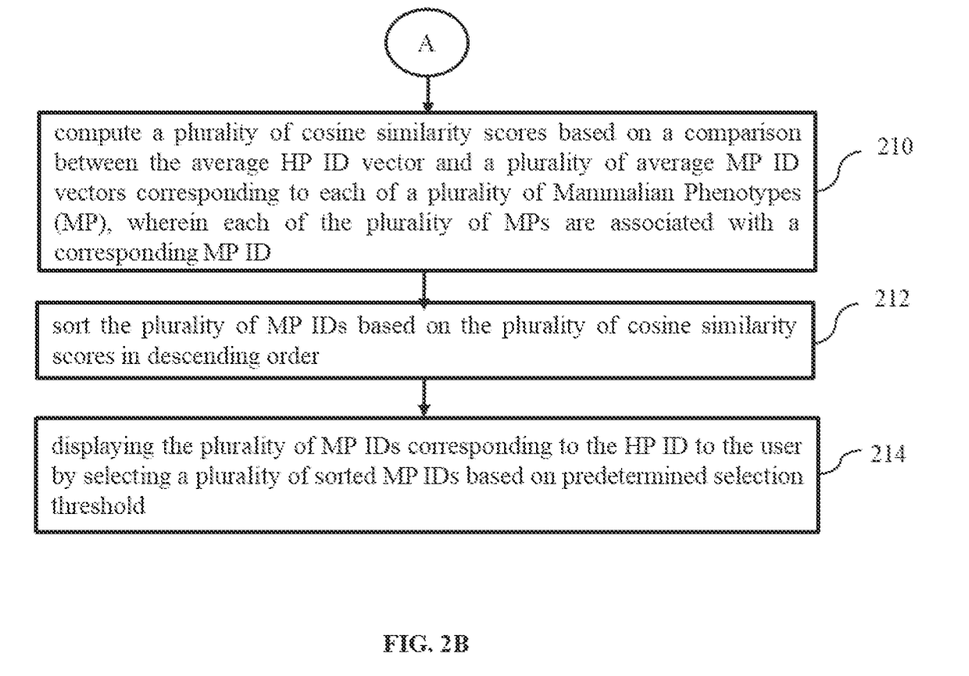

FIGS. 2A and 2B are exemplary flow diagrams illustrating a method 200 for neural document embedding based ontology mapping implemented by the system of FIG. 1 according to some embodiments of the present disclosure. In an embodiment, the system 100 includes one or more data storage devices or the memory 104 operatively coupled to the one or more hardware processor(s) 102 and is configured to store instructions for execution of steps of the method 200 by the one or more hardware processors 102. The steps of the method 200 of the present disclosure will now be explained with reference to the components or blocks of the system 100 as depicted in FIG. 1 and the steps of flow diagram as depicted in FIGS. 2A and 2B. The method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communication network. The order in which the method 200 is described is not intended to be construed as a limitation, and any number of the described method blocks can be combined in any order to implement the method 200, or an alternative method. Furthermore, the method 200 can be implemented in any suitable hardware, software, firmware, or combination thereof.

At step 202 of the method 200, the one or more hardware processors 102 are configured by the programmed instructions to receive a Human Phenotype (HP) Identification number (ID) pertaining to a phenotype associated with a human disease from a user. For example, a plurality of HPs for a plurality of disease and the corresponding ID is shown in Table 1.

TABLE I

| Human disease | Phenotype | HP ID |
|---|---|---|
| DEAFNESS, AUTOSOMAL RECESSIVE 66 | Sensorineural hearing impairment | HP: 0000407 |
| ANOSMIA FOR ISOBUTYRIC ACID | Partial anosmia | HP: 0010633 |
| THORACIC DYSOSTOSIS, ISOLATED | Bell-shaped thorax, Pectus excavatum, Recurrent respiratory infections, Short ribs | HP: 0001591, HP: 0000767, HP: 0002205, HP: 0000773 |

At step 204 of the method 200, the one or more hardware processors 102 are configured by the programmed instructions to compute a first HP ID vector corresponding to the HP ID using a trained word2vec model, wherein the word2vec model is trained using a training corpus.

Figure 3:
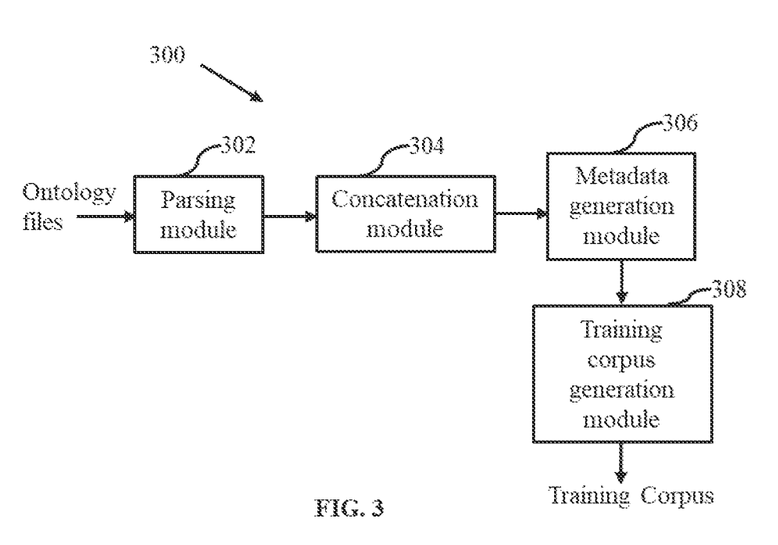
FIG. 3 is functional architecture for generating a training corpus for the processor implemented method for neural document embedding based ontology mapping implemented by the system of FIG. 1, in accordance with some embodiments of the present disclosure.

In an embodiment, the method of generating the training corpus is explained with reference to FIG. 3. FIG. 3 is functional architecture for generating a training corpus for the processor implemented method for neural document embedding based ontology mapping implemented by the system of FIG. 1, in accordance with some embodiments of the present disclosure. Now referring to FIG. 3, the functional architecture includes a parsing module 302, a concatenation module 304, a metadata generation module 306 and a training corpus generation module 308. The parsing module 302 receives the plurality of ontology files. The plurality of ontology files includes the HP ontology file and the MP ontology file. The plurality of ontology files includes a plurality of phenotype names, a definition corresponding to each of the plurality of phenotype names and plurality of synonyms corresponding to each of the plurality of phenotype names. After receiving the plurality of ontology files, the parsing module 302 performs parsing to obtain the plurality of clean ontology files. In parsing, a plurality of word corpus associated with each of the plurality of phenotype ontology files are converted to lowercase and a plurality irrelevant word corpus are removed from the plurality of phenotype ontology files. The concatenation module 304 generates the concatenated data by concatenating each of the plurality of phenotype names, the definition corresponding to each of the plurality of phenotype names and the synonyms corresponding to each of the plurality of phenotype names based on the plurality of clean phenotype ontology files. The metadata generation module 306 generates a plurality of meta data for each of the plurality of phenotype names based on the concatenated data and an article database. The article database includes the article title and the article abstract corresponding to the PUBMED ID corresponding to the phenotype ID. The metadata includes the phenotype ID, the synonym, the corresponding definition, a specific abstract and a related article title. Finally, the training corpus generation module 308 generates the training corpus based on the concatenated data and the plurality of metadata corresponding to each of the plurality of phenotype names. An example training corpus is shown in table II.

mance is measured using the Simple Averaging of the Word Vectors model on the HP-MP mapping task. The word2vec model takes a description of Human/Mouse Phenotype and tokenizes the description into a series of words. Then for each word it gets its corresponding word embedding/vector, takes average of all the word embeddings to get a final embedding representing the phenotype description.

In an embodiment, the two data sets used for finetuning the word2vec model are (i) A corpus which only consists of phenotype descriptions (name+definition) from both human and mouse along with the synonyms for the phenotypes named as "Corpus 1" (ii) A corpus which consists everything that is there in "Corpus 1" along with specific PUBMED abstracts and article titles corresponding to the HP and the MP IDs of human and mouse phenotypes, named as "Corpus 2".

The finetuning is performed in the trained word vectors by training the skip-gram based word2vec model in an unsupervised manner on both Corpus 1 and Corpus 2. The technical parameters of the skip-gram model that are fixed across the finetuning process are: min_count=1, sg=1, hs=0 and size=200. The result of Simple Averaging of word vectors for Corpus 1 and Corpus 2 are given in Table III.

TABLE II

| ID | Name | Definition | Synonym | PubMed ID |
|---|---|---|---|---|
| HP: 0002236 | Frontal upsweep of hair | Upward and/or sideward growth of anterior hair. | Upswept frontal hairline | 19125436 |
| HP: 0002251 | Aganglionic megacolon | An abnormality resulting from a lack of intestinal ganglion cells (i.e., an aganglionic section of bowel) that results in bowel obstruction with enlargement of the colon. | Congenital megacolon | 17965226 |
| MP: 0000044 | absent organ of Corti | absence of the highly specialized epithelium in the floor of the ductus cochlearis | absent acoustic papilla | 10072433 |

In an embodiment, the method of obtaining articles from the plurality of biomedical databases like PUBMED and MEDLINE includes the following steps: Initially, xml files associated with the plurality of biomedical databases are obtained and converted to a SQL database by parsing. The SQL database includes a table with the following columns pubmed_id, an abstract_title and an abstract.

In an embodiment, the method of training the word2vec model is explained as follows: Initially, a plurality of pretrained biomedical word vectors are obtained from a database. Further, an initial training of the word2vec model is performed based on the plurality of pretrained biomedical word vectors. The word2vec model is based on skip gram. Finally, the initially trained word2vec model is finetuned using the training corpus.

In an embodiment, the word2vec model is finetuned to increase mapping accuracy. The finetuning is carried out using two datasets of variable sizes. The size between the datasets is varied to identify difference in performance when there is a change in dataset quality and size. The perfor-

TABLE III

| Corpus | Corpus Size (number of sentences) | Window size | Iterations | Total # of correct HP to MP mapping pairs. |
|---|---|---|---|---|
| Corpus 1 | 94530 | 5 | 10 | 7153 |
| Corpus 1 | 94530 | 3 | 10 | 7022 |
| Corpus 1 | 94530 | 5 | 50 | 7547 |
| Corpus 1 | 94530 | 5 | 100 | 7659 |
| Corpus 1 | 94530 | 5 | 150 | 7651 |
| Corpus 1 | 94530 | 5 | 200 | 7763 |
| Corpus 1 | 94530 | 5 | 300 | 7793 |
| Corpus 2 | 301740 | 5 | 10 | 7541 |
| Corpus 2 | 301740 | 3 | 10 | 7355 |
| Corpus 2 | 301740 | 5 | 50 | 7793 |
| Corpus 2 | 301740 | 5 | 100 | 7870 |
| Corpus 2 | 301740 | 5 | 150 | 7848 |
| Corpus 2 | 301740 | 5 | 200 | 7886 |
| Corpus 2 | 301740 | 5 | 300 | 7865 |

At step 206 of the method 200, the one or more hardware processors 102 are configured by the programmed instructions to simultaneously compute a second HP ID vector corresponding to the HP ID using a trained Doc2vec model, wherein the Doc2vec model is trained using the training corpus.

In an embodiment, the method of training the trainedDoc2vec model is explained as follows: Initially, a plurality of trained word vectors are received. The plurality of trained word vectors are generated using the trained word2vec model. Further, an initial training of the Doc2vec model is performed based on the plurality of trained word vectors, wherein the Doc2vec model is based on distributed bag of words. Finally, the initially trained Doc2vec model is further trained using the training corpus.

In an embodiment, the Corpus 2 and the word vectors finetuned on Corpus 2 corresponding to the window size value 5 and iteration value 200 are utilized as a basis for training Doc2Vec model. The Doc2vec model is trained using PV-DBOW and fixed parameters values used in the models are as follows: vector_size=200, min_count=1, worker_count=1, negative_size=5, seed=42, dm_concat=1, dm=0, sampling_threshold=1e-5 and dbow_words=1.

In an embodiment, in addition to the above mentioned technical parameters, various combination of window size and iteration values are used for training the Doc2Vec model. The Doc2Vec model is evaluated in a similar fashion as the Simple Averaging of Word Vector model. The results for the various Doc2Vec models trained on the Corpus 2 and different value of window size and iterations are given in Table IV. Now referring to table IV, the Doc2Vec model that is trained on the settings where window size value is 5 and the iteration value is 20 is the optimal one.

TABLE IV

| Corpus | Corpus Size (number of sentences) | Window size | Iterations | Total # of correct Hp to MP mapping pairs. |
|---|---|---|---|---|
| Corpus 2 | 301740 | 3 | 50 | 7446 |
| Corpus 2 | 301740 | 3 | 100 | 7496 |
| Corpus 2 | 301740 | 3 | 200 | 7164 |
| Corpus 2 | 301740 | 3 | 500 | 6599 |
| Corpus 2 | 301740 | 5 | 20 | 7802 |
| Corpus 2 | 301740 | 5 | 50 | 7772 |
| Corpus 2 | 301740 | 5 | 100 | 7571 |
| Corpus 2 | 301740 | 5 | 200 | 7261 |
| Corpus 2 | 301740 | 3 | 500 | 6633 |

At step 208 of the method 200, the one or more hardware processors 102 are configured by the programmed instructions to compute an average HP ID vector based on the first HP ID vector and the second HP ID vector.

At step 210 of the method 200, the one or more hardware processors 102 are configured by the programmed instructions to compute a plurality of cosine similarity scores based on a comparison between the average HP ID vector and a plurality of average MP ID vectors corresponding to each of a plurality of Mammalian Phenotypes (MP). Each of the plurality of MPs are associated with a corresponding MP ID. The cosine similarity score between the plurality of HP IDs and the plurality of MP IDs are shown in table V.

TABLE V

| HP ID | MP ID | Similarity Score |
|---|---|---|
| HP: 0004403 | MP: 0003276 | 0.881 |
| HP: 0004403 | MP: 0003321 | 0.860 |
| HP: 0004403 | MP: 0003272 | 0.822 |
| HP: 0004415 | MP: 0010457 | 0.965 |
| HP: 0004415 | MP: 0010475 | 0.944 |
| HP: 0004415 | MP: 0010657 | 0.920 |

In an embodiment, each of the plurality of average MP ID vector is computed based on a first MP ID vector and a second MP ID vector. The first MP ID vector is computed using the trained word2vec model trained using the training corpus. The second MP ID vector is computed using the trained doc2vec model trained using the training corpus.

At step 212 of the method 200, the one or more hardware processors 102 are configured by the programmed instructions to sort the plurality of MP IDs based on the plurality of cosine similarity scores in descending order. For example, the plurality of MP IDs sorted based on the cosine similarity score is shown in Table VI.

TABLE VI

| HP ID | MP ID | Similarity Score |
|---|---|---|
| HP: 0004415 | MP: 0010457 | 0.965 |
| HP: 0004415 | MP: 0010475 | 0.944 |
| HP: 0004415 | MP: 0010657 | 0.920 |
| HP: 0004403 | MP: 0003276 | 0.881 |
| HP: 0004403 | MP: 0003321 | 0.860 |
| HP: 0004403 | MP: 0003272 | 0.822 |

At step 214 of the method 200, the one or more hardware processors 102 are configured by the programmed instructions to display the plurality of MP IDs corresponding to the HP ID to the user by selecting a plurality of sorted MP IDs based on a predetermined selection threshold. In an embodiment, the predetermined selection threshold is 50. In another embodiment, the predetermined selection threshold is determined by the user.

Figure 4:
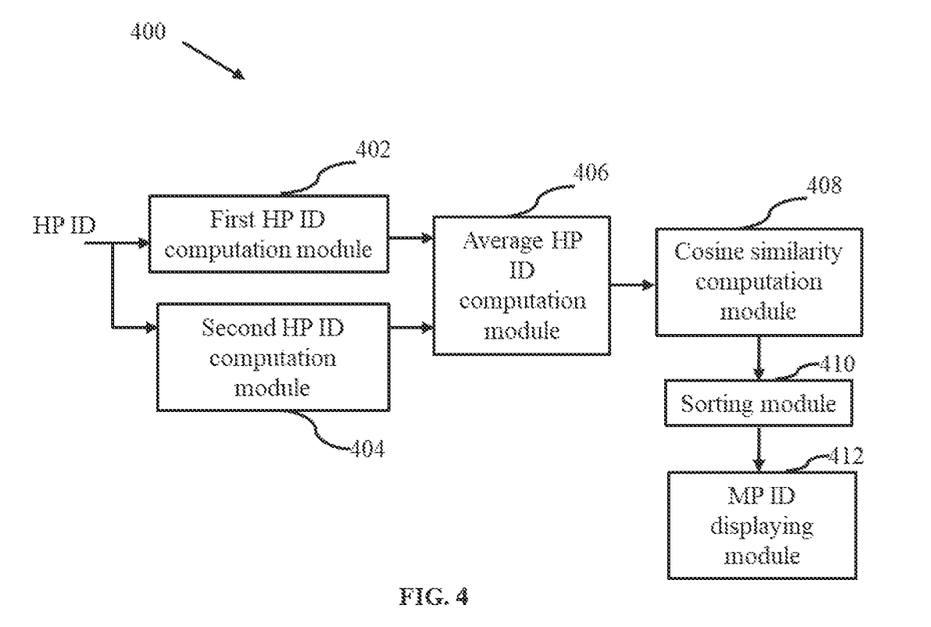
FIG. 4 is an example overall architecture for the processor implemented method for neural document embedding based ontology mapping implemented by the system of FIG. 1, in accordance with some embodiments of the present disclosure.

FIG. 4 is an example overall architecture for the processor implemented method for neural document embedding based ontology mapping implemented by the system of FIG. 1, in accordance with some embodiments of the present disclosure. Now referring to FIG. 4, the overall architecture includes a first HP ID computation module 402, a second HP ID computation module 404, an average HP ID computation module 406, a cosine similarity computation module 408, a sorting module 410, an MP ID displaying module 412. The first HP ID computation module 402 receives the HP ID and computes the first HP ID vector using the trained word2vec model. The second HP ID computation module 404 receives the HP ID and computes the second HP ID vector using the trained Doc2vec model. Further, the average HP ID computation module 406 computes the average HP ID vector based on the first HP ID vector from the first HP ID computation module 402 and the second HP ID vector from the second HP ID computation module 404. Further, the average HP ID vector is compared with the plurality of average MP ID vectors using the cosine similarity computation module 408 to obtain the plurality of cosine similarity scores. The average MP ID is computed based on the first MP Id vector and the second MP ID vector. The first MP ID vector is computed by the trained word2vec model as like the first HP ID vector. The second MP ID vector is computed by the trained Doc2vec model as like the second HP ID vector. The plurality of MP IDs are sorted in descending order based on the plurality of cosine similarity scores by the a sorting module 410. Finally, top n number of MP IDs are selected based on a selection threshold and displayed to the user by the MP ID displaying module 412.

In an embodiment, the present disclosure is experimented as follows: To evaluate the mapping approach, mouse models are prioritized for various diseases from Online Mendelian Inheritance in Man (OMIM). This is done by mapping human disease phenotypes to mouse model phenotypes and ranking the models using the Ensemble approach. To calculate phenotype semantic similarity of human disease phenotypes and mouse model phenotypes, the procedure followed is: For each human phenotype term associated with a given OMIM disease, semantic similarity was calculated for all the phenotype terms associated with a mouse model. For each human phenotype term, mouse term with maximum score formed its best mapped pair. For each phenotype term such pairs were found from a given mouse model. The scores of the pairs were summed and averaged over the number of human phenotypes for a disease giving a final score to the mouse model/gene. The formula for scoring the genes is given in equation 1.

$$\text{Score}(\text{Disease}(D), \text{MammalianGene}(G)) = \sum_{k=1}^{n} \max_{j=1}^{(m)} similarityscore(h_i, m_j)/n, \quad (1)$$

where $h_1 \ldots h_n$ are the 'n' phenotypes associated with the disease D, $m_1 \ldots m_m$ are the 'm' phenotypes associated with the mouse gene. For each OMIM disease top 50 prioritized mouse genes ranked from Ensemble approach are checked for their true association with the disease.

In an embodiment, the cosine similarity score is computed between the plurality of HP IDs taken from hp.obo file and the plurality of MP IDs taken from mp.obo file. The hp.obo file and the mp.obo file are downloaded from Open Biomedical Ontology (OBO) foundry. HPO annotations for rare diseases were taken from phenotype.hpoa file which has 7675 OMIM, 47 DECIPHER and 3889 ORPHANET data sets. The present disclosure utilized HPO annotations for each of the OMIM IDs for the analysis from phenotype.hpoa file and performed filteration on aspect value wherein the only entries having aspect value as 'P' is selected, wherein P refers to phenotype. Further MPO annotations are taken from MGI_GenePheno.rpt file. This file contains genotypes and MP annotations for genes excluding conditional mutations in a tab-delimited format. This file is used to retrieve the MP IDs for corresponding mouse models. The phenotypes and disease annotation for genes, excluding conditional mutations in tab-delimited format are taken from MGI_Geno_DiseaseDO.rpt file. This file is used to get the relevant mouse genes for the OMIM IDs. The DOID IDs, disease name and descriptions and other information such as the corresponding OMIM IDs for the DOID (Disease Ontology Identifiers) ID are taken from doid.obo file. The accuracy of the present disclosure is illustrated in the table VII.

TABLE VII

| Disease Set | Number of OMIM IDs | % of hits by present disclosure |
| --- | --- | --- |
| Immune System | 51 | 65 |
| Cardiovascular System | 69 | 70 |
| Inherited Metabolic Diseases | 155 | 38 |
| Endocrine System | 50 | 54 |
| Gastrointestinal System | 39 | 69.2 |
| Hematopoietic System | 59 | 61 |
| Integumentary System | 40 | 45 |
| Urinary System | 40 | 67.5 |
| Developmental Disorder of Mental Health | 83 | 6 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address the unresolved problem of mapping two ontologies without bridging ontology. Here, the mapping without bridging ontologies achieved by an ensemble model comprising the word2vec model and the Doc2vec model trained using a unique training corpus. The training corpus is generated using a HP and MP ontology files. The HP and MP ontology files are cleaned using parsing and further a concatenated file is created and the concatenated file is enriched based on the corresponding articles obtained from the PUBMED and MEDLINE database. The training corpus is generated based on the concatenated data enriched with PUBMED and MEDLINE dataset. Finally, the similarity score is computed using cosine similarity. The unique training corpus and the ensemble model provides enhances accuracy to the present disclosure.

It is to be understood that the scope of the protection is extended to such a program and in addition to a computer-readable means having a message therein such computer-readable storage means contain program-code means for implementation of one or more steps of the method when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs, GPUs and edge computing devices.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e. non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, the method comprising:
   receiving, by one or more hardware processors, a Human Phenotype (HP) Identification number (ID) pertaining to a phenotype associated with a human disease from a user;
   computing, by the one or more hardware processors, a first HP ID vector corresponding to the HP ID using a trained word2vec model, wherein the word2vec model is trained using a training corpus;
   simultaneously computing, by the one or more hardware processors, a second HP ID vector corresponding to the HP ID using a trained Doc2vec model, wherein the Doc2vec model is trained using the training corpus;
   computing, by the one or more hardware processors, an average HP ID vector based on the first HP ID vector and the second HP ID vector;
   computing, by the one or more hardware processors, a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID;
   sorting, by the one or more hardware processors, the plurality of MP IDs based on the plurality of cosine similarity scores in descending order; and
   displaying, by the one or more hardware processors, the plurality of MP IDs corresponding to the HP ID to the user by selecting a plurality of sorted MP IDs based on a predetermined selection threshold.

2. The processor implemented method of claim 1, wherein the training corpus is generated by:
   receiving a plurality of ontology files, wherein the plurality of ontology files comprises a HP Ontology (HPO) file and a MP Ontology (MPO) file, wherein the plurality of ontology files comprises a plurality of phenotype names, a definition corresponding to each of the plurality of phenotype names and plurality of synonyms corresponding to each of the plurality of phenotype names;
   generating a plurality of clean phenotype ontology files by parsing each of the plurality of phenotype ontology files, wherein a plurality of word corpus associated with each of the plurality of phenotype ontology files are converted to lowercase, and wherein a plurality irrelevant word corpus are removed from the plurality of phenotype ontology files;
   generating a concatenated data by concatenating each of the plurality of phenotype names, the definition corresponding to each of the plurality of phenotype names and the synonyms corresponding to each of the plurality of phenotype names based on the plurality of clean phenotype ontology files;
   generating a plurality of meta data for each of the plurality of phenotype names based on the concatenated data and an article database, wherein the article database comprises an article title and an article abstract corresponding to a phenotype ID, wherein the metadata comprises the phenotype ID, a synonym, the corresponding definition, a specific abstract and a related article title; and
   generating the training corpus based on the concatenated data and the plurality of metadata corresponding to each of the plurality of phenotype names.

3. The processor implemented method of claim 1, wherein the method of pretraining the word2vec model using the training corpus comprises:
   obtaining a plurality of pretrained biomedical word vectors from a database;
   performing an initial training of the word2vec model based on the plurality of pretrained biomedical word vectors, wherein the word2vec model is based on skip gram; and
   finetuning the initially trained word2vec model using the training corpus.

4. The processor implemented method of claim 1, wherein the method of pretraining the doc2vec model using the training corpus comprises:
   receiving a plurality of trained word vectors, wherein the plurality of trained word vectors are generated using the trained word2vec model;

performing an initial training of the Doc2vec model based on the plurality of trained word vectors, wherein the Doc2vec model is based on distributed bag of words; and training the initially trained Doc2vec model using the training corpus.

5. The processor implemented method of claim 1, wherein each of the plurality of average MP ID vector is computed based on a first MP ID vector and a second MP ID vector.

6. The processor implemented method of claim 1, wherein the first MP ID vector is computed using the trained word2vec model trained using the training corpus.

7. The processor implemented method of claim 1, wherein the second MP ID vector is computed using the trained doc2vec model trained using the training corpus.

8. A system comprising:
at least one memory storing programmed instructions; one or more Input/Output (I/O) interfaces; and one or more hardware processors operatively coupled to the at least one memory, wherein the one or more hardware processors are configured by the programmed instructions to:
receive a Human Phenotype (HP) Identification number (ID) pertaining to a phenotype associated with a human disease from a user;
compute a first HP ID vector corresponding to the HP ID using a trained word2vec model, wherein the word2vec model is trained using a training corpus;
simultaneously compute a second HP ID vector corresponding to the HP ID using a trained Doc2vec model, wherein the Doc2vec model is trained using the training corpus;
compute an average HP ID vector based on the first HP ID vector and the second HP ID vector;
compute a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID;
sort the plurality of MP IDs based on the plurality of cosine similarity scores in descending order; and
display the plurality of MP IDs corresponding to the HP ID to the user by selecting a plurality of sorted MP IDs based on a predetermined selection threshold.

9. The system of claim 8, wherein the training corpus is generated by:
receiving a plurality of ontology files, wherein the plurality of ontology files comprises a HP Ontology (HPO) file and a MP Ontology (MPO) file, wherein the plurality of ontology files comprises a plurality of phenotype names, a definition corresponding to each of the plurality of phenotype names and plurality of synonyms corresponding to each of the plurality of phenotype names;
generating a plurality of clean phenotype ontology files by parsing each of the plurality of phenotype ontology files, wherein a plurality of word corpus associated with each of the plurality of phenotype ontology files are converted to lowercase, and wherein a plurality irrelevant word corpus are removed from the plurality of phenotype ontology files;
generating a concatenated data by concatenating each of the plurality of phenotype names, the definition corresponding to each of the plurality of phenotype names and the synonyms corresponding to each of the plurality of phenotype names based on the plurality of clean phenotype ontology files;
generating a plurality of meta data for each of the plurality of phenotype names based on the concatenated data and an article database, wherein the article database comprises an article title and an article abstract corresponding to a phenotype ID, wherein the metadata comprises the phenotype ID, a synonym, the corresponding definition, a specific abstract and a related article title; and
generating the training corpus based on the concatenated data and the plurality of metadata corresponding to each of the plurality of phenotype names.

10. The system of claim 8, wherein the method of pretraining the word2vec model using the training corpus comprises:
obtaining a plurality of pretrained biomedical word vectors from a database;
performing an initial training of the word2vec model based on the plurality of pretrained biomedical word vectors, wherein the word2vec model is based on skip gram; and
finetuning the initially trained word2vec model using the training corpus.

11. The system of claim 8, wherein the method of pretraining the doc2vec model using the training corpus comprises:
receiving a plurality of trained word vectors, wherein the plurality of trained word vectors are generated using the trained word2vec model;
performing an initial training of the Doc2vec model based on the plurality of trained word vectors, wherein the Doc2vec model is based on distributed bag of words; and
training the initially trained Doc2vec model using the training corpus.

12. The system of claim 8, wherein each of the plurality of average MP ID vector is computed based on a first MP ID vector and a second MP ID vector.

13. The system of claim 8, wherein the first MP ID vector is computed using the trained word2vec model trained using the training corpus.

14. The system of claim 8, wherein the second MP ID vector is computed using the trained doc2vec model trained using the training corpus.

15. One or more non-transitory machine-readable information storage mediums comprising one or more instructions which when executed by one or more hardware processors cause:
receiving a Human Phenotype (HP) Identification number (ID) pertaining to a phenotype associated with a human disease from a user;
computing a first HP ID vector corresponding to the HP ID using a trained word2vec model, wherein the word2vec model is trained using a training corpus;
simultaneously computing a second HP ID vector corresponding to the HP ID using a trained Doc2vec model, wherein the Doc2vec model is trained using the training corpus;
computing an average HP ID vector based on the first HP ID vector and the second HP ID vector;
computing a plurality of cosine similarity scores based on a comparison between the average HP ID vector and a plurality of average MP ID vectors corresponding to each of a plurality of Mammalian Phenotypes (MP), wherein each of the plurality of MPs is associated with a corresponding MP ID;

sorting the plurality of MP IDs based on the plurality of cosine similarity scores in descending order; and displaying the plurality of MP IDs corresponding to the HP ID to the user by selecting a plurality of sorted MP IDs based on a predetermined selection threshold.

16. The one or more non-transitory machine-readable information storage mediums of claim 15, wherein the training corpus is generated by:

receiving a plurality of ontology files, wherein the plurality of ontology files comprises a HP Ontology (HPO) file and a MP Ontology (MPO) file, wherein the plurality of ontology files comprises a plurality of phenotype names, a definition corresponding to each of the plurality of phenotype names and plurality of synonyms corresponding to each of the plurality of phenotype names;

generating a plurality of clean phenotype ontology files by parsing each of the plurality of phenotype ontology files, wherein a plurality of word corpus associated with each of the plurality of phenotype ontology files are converted to lowercase, and wherein a plurality irrelevant word corpus are removed from the plurality of phenotype ontology files;

generating a concatenated data by concatenating each of the plurality of phenotype names, the definition corresponding to each of the plurality of phenotype names and the synonyms corresponding to each of the plurality of phenotype names based on the plurality of clean phenotype ontology files;

generating a plurality of meta data for each of the plurality of phenotype names based on the concatenated data and an article database, wherein the article database comprises an article title and an article abstract corresponding to a phenotype ID, wherein the metadata comprises the phenotype ID, a synonym, the corresponding definition, a specific abstract and a related article title; and generating the training corpus based on the concatenated data and the plurality of metadata corresponding to each of the plurality of phenotype names.

17. The one or more non-transitory machine-readable information storage mediums of claim 15, wherein the method of pretraining the word2vec model using the training corpus comprises:

obtaining a plurality of pretrained biomedical word vectors from a database;

performing an initial training of the word2vec model based on the plurality of pretrained biomedical word vectors, wherein the word2vec model is based on skip gram; and finetuning the initially trained word2vec model using the training corpus.

18. The one or more non-transitory machine-readable information storage mediums of claim 15, wherein the method of pretraining the doc2vec model using the training corpus comprises:

receiving a plurality of trained word vectors, wherein the plurality of trained word vectors are generated using the trained word2vec model;

performing an initial training of the Doc2vec model based on the plurality of trained word vectors, wherein the Doc2vec model is based on distributed bag of words; and training the initially trained Doc2vec model using the training corpus.

19. The one or more non-transitory machine-readable information storage mediums of claim 15, wherein each of the plurality of average MP ID vector is computed based on a first MP ID vector and a second MP ID vector.

20. The one or more non-transitory machine-readable information storage mediums of claim 15, wherein the first MP ID vector is computed using the trained word2vec model trained using the training corpus.

* * * * *